United States Patent [19]

Wurmb et al.

[11] 3,957,927

[45] May 18, 1976

[54] MANUFACTURE OF PHOSPHORUS NITRIDE ESTERS

[75] Inventors: Rolf Wurmb, Heidelberg; Dietmar Werner, Weisenheim; Gerd Wunsch, Speyer; Volker Kiener; Wolfgang Schwarz, both of Ludwigshafen, all of Germany

[73] Assignee: BASF Aktiengesellschaft, Ludwigshafen (Rhine), Germany

[22] Filed: July 2, 1974

[21] Appl. No.: 485,073

[30] Foreign Application Priority Data

July 3, 1973 Germany............................. 2333746

[52] U.S. Cl............................. 260/973; 260/927 N; 427/394; 428/921
[51] Int. Cl.² ........................................... C07F 9/21
[58] Field of Search ...................... 260/927 M, 973

[56] References Cited

UNITED STATES PATENTS

| | | | |
|---|---|---|---|
| 2,586,312 | 2/1952 | Dishon et al................ | 260/927 N X |
| 3,795,526 | 3/1974 | Bergeron .................... | 260/927 N X |

*Primary Examiner*—Anton H. Sutto
*Attorney, Agent, or Firm*—Johnston, Keil, Thompson & Shurtleff

[57] ABSTRACT

Cyclic phosphorus nitride esters are prepared as flameproofers of high durability for use on regenerated cellulose. The known synthesis from cyclic phosphorus nitride chlorides with alcohols in the presence of amines is controlled under specific temperature conditions such that desired side-reactions permit the production, in a simple manner and in very high yields, of products showing a durability to washing not hitherto achieved.

3 Claims, No Drawings

MANUFACTURE OF PHOSPHORUS NITRIDE ESTERS

It is well known that phosphorus nitride esters may be prepared by reacting phosphorus nitride chlorides with alcohols in the presence of, say, pyridine and at temperatures of from 0° to 5°C and that these products may be used as flameproofers. These flameproofers are highly suitable for use on regenerated cellulose, since they have no substantial influence on the strength of the fibers even at high rates of application and also cause no change in the dyeability of the cellulose material or in its resistance to ultraviolet light.

Despite these advantages, said flameproofers have certain drawbacks. It is often difficult to disperse them satisfactorily in the spinning solution and they are extracted from the fibers by frequent washing (about 40 to 50 washes) to such an extent that the content thereof in the fibers falls below the flameproofing threshold.

It has been shown that higher molecular weight (highly viscous) linear alkoxy phosphazenes, which may be prepared by reacting cyclohexane-insoluble phosphorus nitride chlorides with alcohols and which would be expected to give a high durability to washing due to their lower rate of migration in the regenerated cellulose resulting from the higher molecular weight, are virtually impossible to incorporate in the regenerated cellulose.

It is an object of the present invention to provide an economical process for the preparation of washproof flameproofers for use on regenerated cellulose and to provide a method of flameproofing regenerated cellulose in a simple, economical and wash-resistant manner without impairing the mechanical and other properties of the said regenerated cellulose.

We have now found that these objects may be achieved in a process for the preparation of phosphorus nitride esters serving as flameproofing agents of high wash resistance for use on regenerated cellulose by reacting cyclic phosphorus nitride chlorides of the formula: $(NPCl_2)_{3-8}$ with equivalent amounts of aliphatic alcohols in the presence of tertiary amines and working up by known methods, wherein saturated or unsaturated, straight-chain or branched-chain primary alcohols, which may bear chlorine or bromine or ether, keto or tertiary amino groups or other inert groups and which, in the case of alcohol mixtures, contain on average from 2 to 6 carbon atoms, are reacted in the presence of pyridine or triethylamine by first reacting from 10 to 80% of the equivalent amount of alcohol for from about 1 to 5 hours with the phosphorus nitride chloride at from 10° to 50°C and then adding alcohol in an excess of from 10 to 100% and continuing the reaction at from 10° to 50°C and finally completing the reaction by heating to from 50° to 100°C. The resulting phosphorus nitride esters are dispersed in a regenerated cellulose spinning solution as finely as possible by known methods, whereupon the solution is spun.

Particularly suitable regenerated celluloses are those based on xanthates, and also cuprammonium rayon.

The phosphorus nitride chlorides suitable for use as starting materials in the preparation of the phosphorus nitride esters (or alkoxy phosphazenes — for the nomenclature see S. Pantal and M. Becke-Göhring "6- and 8-gliedrige Ringsysteme in der PhosphorStickstoffchemie", Springer-Verlag, Heidelberg, (1969) for use in the present invention have the general formula $(PNCl_2)_n$. They are prepared by known methods (cf. for example G. Wunsch, R. Schiedermeier, V. Keiner, E. Fluck and G. Heckmann, Chem. Ztg. 94, 1970, p. 832; German Published Application 1,918,697). They are cyclic in nature and n denotes integers of from 3 to 8 inclusive and is mainly 3 or 4. For economical reasons, rings of different sizes are advantageously contained in the mixture obtained in the manufacture of the phosphorus nitride chloride. This mixture is made up approx. as follows:

65–66% of $(NPCl_2)_3$
23% of $(NPCl_2)_4$
6% of $(NPCl_2)_5$
3% of $(NPCl_2)_6$
1.5% of $(NPCl_2)_7$
0.5% of $(NPCl_2)_8$ and about 0.5% of linear polymers. The composition of the oligomer mixture is of no importance as regards the effect achieved. For example, the pure trimer $[NP(OR)_2]_3$ could be used if it were not prohibitive for economical reasons. These phosphorus nitride chlorides are reacted in stages with, in all, equivalent amounts of saturated or olefinically unsaturated, straight-chain or branched-chain, primary alcohols, which may bear chlorine or bromine or ether, keto or tertiary amino groups or other inert groups and which contain from 2 to 6 and preferably 3 carbon atoms, with the elimination of hydrogen chloride and formation of phosphorus nitride esters according to the equation:

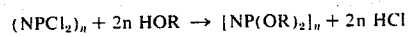

$$(NPCl_2)_n + 2n\ HOR \rightarrow [NP(OR)_2]_n + 2n\ HCl$$

It is also possible to use mixtures of different monovalent primary alcohols. Suitable alcohols are for example n-propanol, n-butanol, isobutanol, methyl glycol, 2,3-dibromopropanol, 3-N,N-dimethylaminopropanol, allyl alcohol and crotyl alcohol. Where alcohol mixtures are used, these may contain a portion of methanol and of alcohols of up to 12 carbon atoms and preferably of up to 8 carbon atoms. In such cases, the number of carbon atoms given (from 2 to 6 and preferably 3) is an average value. Phosphorus nitride esters of alcohols of, on average, less than 3 carbon atoms tend to be more water-soluble and this manifests itself in unfavorable rates of incorporation during spinning and in unsatisfactory wash resistance of the flameproof finish. On the other hand, if the alcohols contain, on average, considerably more than 3 carbon atoms, the flameproofer has a lower content of phosphorus and thus shows diminished efficiency. The reaction takes place in the presence of excess alcohol (from 10 to 100% and preferably from 20 to 70% excess) and excess tertiary amine, preferably triethylamine and in particular pyridine. The "molar" ratio of $NPCl_2$ (here regarded as a molecule although it is in fact oligomeric) to pyridine is advantageously from 1:2.4 to 1:3.5. The use of inert solvents during the reaction is possible but usually of no added advantage. Conveniently, the reaction is carried out in the mixture of tertiary amine and alcohol serving as solvents.

In the first reaction stage, from 10 to 80% and preferably from 30 to 60% of the equivalent amounts of alcohol are reacted with the phosphorus nitride chloride and the amine at from 10° to 50° and preferably from 15° to 25°C for from 1 to 6 hours and preferably from 2 to 4 hours. By "equivalent" amounts of alcohol we mean one mole of alcohol per mole of chlorine in the phosphorus nitride chloride. Advantageously, the required amount of alcohol for the first stage is added to a 5–41% and preferably 25–33% solution of phosphorus nitride chloride in pyridine in the said temperature range. In the second stage, the remaining alcohol is added and the mixture is held at from 10° to 50°C and preferably 25° to 45°C and is then heated, in the third stage, to from 50° to 100° and preferably from 60° to 80° to complete the reaction. The second and third stages have a total residence time of from about 5 to 15 hours and preferably from 7 to 10 hours, of which from about 30 minutes to 6 hours fall to the third stage.

30 minutes to 6 hours fall to the third stage.

Working up is effected in known manner, for example by the neutralizing method or the steaming method.

In the neutralizing method, excess pyridine is converted to the salt by means of an inorganic acid, particularly hydrochloric acid, and the phosphorus nitride ester is extracted from the aqueous phase by an organic solvent such as hexane, heptane or benzene. Evaporation of the solvent leaves the pure phosphorus nitride ester.

In the steaming method, excess pyridine and excess alcohol are separated from the reaction mixture. The steaming method may be carried out in various ways. In one method, steam may be directly blown into the reaction mixture and in another method water may be added to the reaction mixture and excess alcohol and pyridine are distilled off with some of the water. Further working up is then effected by extraction as in the neutralizing method.

Another working up method consists in adding diethyl ether to the reaction mixture, filtering off the precipitated pyridine hydrochloride, washing the filtrate with water, dilute hydrochloric acid, sodium bicarbonate solution and again with water and then drying. The ether is removed and the phosphorus nitride ester is distilled in vacuo.

When working up is complete, there is obtained a phosphorus nitride ester mixture which consists not only of rings of different sizes but also of separate rings and rings which are joined together to different extents. This oily mixture having a viscosity of from 400 to 5,000 centistokes and preferably from 1,100 to 3,300 centistokes is an excellent flameproofer for regenerated cellulose of previously unknown wash resistance. The requirements of German Standard DIN 53,906 are still met after 50 boils. It is obtained in yields of more than 95% of theory. It also satisfies all requirements as regards residual chlorine content, acid number, color number and viscosity and, as far as is known, these advantages are offset by virtually no drawbacks.

The flameproofers to be used in the invention are incorporated in the regenerated cellulose by finely dispersing or emulsifying the flameproofer in the aqueous cellulose xanthate solution and precipitating said solution in the usual manner in the form of filaments or sheeting by extrusion into acid precipitating baths. It is an advantage that the oily phosphorus/nitrogen compounds to be used in the invention are readily dispersed in the solutions of the cellulose material, if necessary with the use of conventional dispersing agents such as polyalkylene glycols or amines such as triisopropanolamine. They may be added as oil or as a concentrated emulsion in cellulose solution.

The flameproofers are enclosed in the precipitated cellulose to a very high extent (up to 95%). This is surprising, particularly in view of the very poor rates of incorporation of the more viscous products prepared by esterification of linear phosphorus nitride dichlorides with monovalent alcohols. The flameproofers are applied at rates giving a content of flamproofer in the cellulose of from 5 to 30% and preferably from 8 to 25% by weight of the weight of cellulose treated.

The cellulose material treated according to the present invention is distinguished by its excellent flame resistance. It extinguishes immediately when the flame is removed therefrom (burning period as measured according to DIN 53,906 is 0 sec.). It is great advantage that the other properties of the cellulose material or the filaments or fibers, such as the natural whiteness, dyeability, handle and washability, are virtually unchanged as compared with unmodified regenerated cellulose material. Another advantage is that the tensile strength and attrition resistance of the filaments are virtually no lower than in the case of unmodified filaments. However, the special advantage lies in the high wash resistance of the finish compared with cellulose flameproofed by prior art methods.

The process may be carried out batchwise or, preferably, continuously.

In the following Examples the parts and percentages are by weight.

EXAMPLE 1

250 parts/hr of pyridine and 112.5 parts of phosphorus nitride chloride in the form of the isomer mixture obtained in the synthesis described in the above reference and 65 parts/hr of n-propanol (56% of the theoretical amount) are fed, at 20°C, to the first stage of a continuously operated cascade of stirred vessels.

The average residence time is 4 hours in the first stage. 140 parts/hr of n-propanol are fed, at 40°C, to a second stage. The average residence time in this stage is also 4 hours.

The reaction solution is then heated to 70°C to complete the reaction. The average residence time at this temperature is 5 hours.

Working up is effected in a subsequent stirred vessel, in which the solution is acidified with 500 parts/hr of 10% hydrochloric acid at 25°C and the resulting phosphorus nitride ester is extracted by simultaneous addition of 127.5 parts/hr of hexane.

After separation of the organic phase, this is washed with aqueous soda solution.

The hexane solution is evaporated to give, on average, 138.0 parts/hr of phosphorus nitride ester.

The phosphorus content of the ester is 21.3% (equivalent to 97.5% phosphorus yield based on phosphorus in $(NPCl_2)$). $NP(OC_3H_7)_2$ requires a phosphorus content of 19.0%. The difference is due to ring fusion (via oxygen bridges) with the elimination of propyl chloride.

EXAMPLE 2

48 parts of n-propanol (40% of the theoretical amount) are fed, with stirring, to a solution of 200 parts of pyridine and 112.5 parts of phosphorus nitride chloride over 3 hours.

The mixture is then heated to 25°C and 132 parts of n-propanol are added over 4 hours.

The reaction mixture is then heated at 80°C for a further 6 hours.

The reaction mixture is allowed to cool to 25°C and is then acidified with 400 parts of 10% hydrochloric acid, and the phosphorus nitride ester is extracted with 140 parts of hexane.

After separation of the organic extract and removal of the solvent, there are obtained 135.8 parts of phosphorus nitride ester The phophorus content of the ester is 21.7% (equivalent to 98% phosphorus yield based on phosphorus in (NPCl$_2$)).

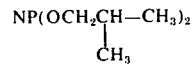

requires 17.0% of phosphorus. The difference is due to ring fusion with the elimination of butyl chloride.

TABLE

| Ester of Example | Yield [%] | Phosphorus content [%] | Residual chlorine content [%] | Viscosity [centistokes] | Av. mol. wt. | Phosphorus content of fibers | | |
|---|---|---|---|---|---|---|---|---|
| | | | | | | prior to boiling [%] | after 25 boils [%] | after 50 boils [%] |
| 1 | 98.5 | 21.3 | 1.0 | 2,100 | 1,070 | 3.5 | 3.4 | 3.4 |
| 2 | 98.0 | 21.7 | 1.1 | 2,900 | 1,100 | 3.4 | 3.3 | 3.3 |
| 3 | 96.5 | 18.6 | 1.2 | 2,400 | 1,300 | 3.4 | 3.3 | 3.2 |
| prior art ester+ (NP(OC$_3$H$_7$)$_2$)$_{3-8}$ | 80.6 | 19.1 | 0.9 | 220 | 590 | 2.8 | 2.6 | 2.4 |

In Example 3, 24% w/w (based on α-cellulose) of phosphorus nitride ester was added to the viscous solution, in the other Examples (Examples 1, 2 and Comparative Example) this figure was 20%.
+similar to that described B. W. Fitzsimmons and R. A. Shaw in J. Chem. Soc. (1964), 1739.

EXAMPLE 3

250 parts/hr of pyridine and 112.5 parts/hr of phosphorus nitride chloride and 51 parts/hr of isobutanol (40% of the theoretical amount) are fed, at 22°C, to the first stage of a continuously operated cascade of stirred vessels.

The average residence time in the first stage is 4.5 hours.

139 parts/hr of isobutanol are fed to a second stage at 45°C, the average residence time being 5 hours.

The reaction solution is then heated to 80°C to complete the reaction. The average residence time at this temperature is 5 hours.

Working up is effected in a subsequent stirred vessel in which the solution is acidified at 25°C by the addition of 500 parts/hour of 10% aqueous hydrochloric acid and the resulting phosphorus nitride ester is extracted by simultaneous addition of 140 parts/hr of hexane.

After separation of the organic phase, this is washed with aqueous soda solution.

The hexane solution is evaporated to give, on average, 156 parts/hr of phosphorus nitride ester.

The phosphorus content of this ester is 18.6% (equivalent to 96.5% phosphorus yield based on phosphorus in the phosphorus nitride chloride.

We claim:

1. A process for the manufacture of phosphorus nitride esters serving as flameproofing agents of high wash resistance for use on regenerated cellulose which comprises: reacting cyclic phosphorus nitride chlorides of the formula: (NPCl$_2$)$_{3-8}$ with equivalent amounts of saturated or ethylenically unsaturated, straight-chain or branched-chain primary alcohols of from 2 to 6 carbon atoms or with mixtures of primary alcohols which contain an average of from 2 to 6 carbon atoms, are reacted in the presence of pyridine or triethylamine by first reacting from 10 to 80% of the equivalent amount of alcohol for from about 1 to 5 hours with the phosphorus nitride chloride at from 10° to 50°C and then adding alcohol in an excess of from 10 to 100% and continuing the reaction at from 10° to 50°C and finally completing the reaction by heating to from 50° to 100°C.

2. A process as set forth in claim 1 wherein said alcohol has three carbon atoms.

3. A process as set forth in claim 1 wherein said alcohol is selected from the groups consisting of n-propanol, n-butanol, isobutanol, methyl glycol, 2,3-dibromopropanol, 3-N,N-dimethylamino-propanol, allyl alcohol and crotyl alcohol.

* * * * *